(12) United States Patent
Fernandez Camacho et al.

(10) Patent No.: US 7,960,025 B2
(45) Date of Patent: Jun. 14, 2011

(54) MAGNETIC NANOPARTICLES COMPRISING A CORE FORMED FROM NOBLE METALS

(75) Inventors: M' Asunción Fernandez Camacho, Seville (ES); Rocio Litran Ramos, Seville (ES); Teresa Cristina Rojas Ruiz, Seville (ES); Juan Carlos Sanchez Lopez, Seville (ES); Antonio Hernando Grande, Madrid (ES); Patricia Crespo Del Arco, Madrid (ES); Blanca Sampedro Rozas, Madrid (ES)

(73) Assignees: Consejo Superior De Investigaciones Cientificas, Madrid (ES); Universidad Complutense De Madrid, Madrid (ES)

( * ) Notice: Subject to any disclaimer, the term of this patent is extended or adjusted under 35 U.S.C. 154(b) by 636 days.

(21) Appl. No.: 11/525,119

(22) Filed: Sep. 22, 2006

(65) Prior Publication Data
US 2007/0151631 A1 Jul. 5, 2007

Related U.S. Application Data

(63) Continuation of application No. PCT/ES2005/070035, filed on Mar. 23, 2005.

(30) Foreign Application Priority Data

Mar. 25, 2004 (ES) .................................. 200400735

(51) Int. Cl.
*B32B 5/16* (2006.01)
*B05D 7/00* (2006.01)
(52) U.S. Cl. ........ 428/403; 427/128; 427/130; 427/216; 977/773; 977/810; 977/838; 977/925; 977/953; 977/960

(58) Field of Classification Search .................. 428/403; 427/212, 128, 130, 216; 977/773, 810, 838, 977/925, 953, 960
See application file for complete search history.

(56) References Cited

U.S. PATENT DOCUMENTS

| 5,294,369 | A  | * | 3/1994 | Shigekawa et al. | ............. | 516/97 |
| 6,730,400 | B1 | * | 5/2004 | Komatsu et al. | ............. | 428/403 |
| 6,923,923 | B2 | * | 8/2005 | Cheon et al. | .................. | 252/512 |
| 6,929,675 | B1 | * | 8/2005 | Bunge et al. | .................... | 75/362 |

FOREIGN PATENT DOCUMENTS

| EP | 1 211 698 A1 | 6/2002 |
| EP | 1 323 793 | 7/2003 |

(Continued)

OTHER PUBLICATIONS

Crespo et all, Permanent Magnetism, Magnetic Anisotropy, and Hysteresis of Thiol-Capped Gold Nanoparticles, Phys. Rev. Lett., vol. 93, No. 8, Aug. 20, 2004, 087204.*

(Continued)

*Primary Examiner* — H. (Holly) T Le
(74) *Attorney, Agent, or Firm* — Wenderoth, Lind & Ponack, L.L.P.

(57) ABSTRACT

The invention relates to nanoparticles of noble metals, having a controlled microstructure which leads to the appearance of ferromagnetic behaviour in said nanoparticles, thereby enabling the use of very small magnets (<5 nm) in a range in which standard ferromagnetic metals behave as superparamagnetic entitles (disappearance of hysteresis cycle). The inventive nanoparticles can be used, for example, to reduce the dimensions in magnetic recordings, as well as in biomedicine as tools for biomolecule recognition, nuclear magnetic resonance imaging, drug-release control or hypothermia treatments.

23 Claims, 7 Drawing Sheets

FOREIGN PATENT DOCUMENTS

| | | |
|---|---|---|
| EP | 1 339 075 A1 | 8/2003 |
| JP | 2003-132519 | 5/2003 |
| WO | 97/24224 | 7/1997 |
| WO | 01/25316 | 4/2001 |
| WO | 01/73123 | 10/2001 |
| WO | 02/18643 | 3/2002 |
| WO | 02/32404 | 4/2002 |
| WO | 03/035829 | 5/2003 |
| WO | 03/057175 | 7/2003 |
| WO | 03/072830 | 9/2003 |

OTHER PUBLICATIONS

Wuelfing et al., Nanometer Gold Clusters Protected by Surface-Bound Monolayers of Thiolated Poy(ethylene glycol) Polymer Electrolyte, J. Am. Chem. Soc. (1998), 120, 12696-12697.*

Maurat et al, Thermal Properties of open-shell metal clusters, New J. Phys., vol. 11, No. 10 (2009) 103031.*

Takano, N., et al., Effect of Copious Vacancies on Magnetism of Pd. Solid State Communications. vol. 97, No. 2. Great Britain. Elsevier Science Ltd. 1996. pp. 153-156.

Sampedro, B., et al. Ferromagnetism in fcc Twinned 2.4 nm Size Pd Nanoparticles. Physical Review Letters. vol. 91, No. 23. The American Physical Society. Dec. 5, 2003. pp. 237203-1-237203-4.

Shinohara, T., and Sato, T. Surface ferromagnetism of Pd Fine Particles. Physical Review Letters. vol. 91, No. 19. The American Physical Society. Nov. 7, 2003. pp. 197201-1-197201-4.

Taniyama, T., Ohta, E., Sato, T. Ferromagnetism of Pd fine particles. Physica B. 1997. pp. 286-288.

Huger, E., Osuch, K. Ferromagnetism in hexagonal close-packed Pd. Europhysics Letters. vol. 63, No. 1. Jul. 1, 2003. pp. 90-96.

Kumar, Vijay, Kawazoe, Yoshiyuki. Icosahedral growth, magnetic behavior, and adsorbate-induced metal-nonmetal transition in palladium clusters. Physical Review B. vol. 66. 2002. pp. 144413-1-144413-11.

Hori, H. et al. Magnetic properties of nano-particles of Au, Pd and Pd/Ni alloys. Journal of Magnetism and Magnetic Materials. 2001. pp. 1910-1911.

Ravel, B., Carpenter, E.E., Harris, V.G. Oxidation of iron in iron/gold core/shell nanoparticles. Journal of Applied Physics. vol. 91, No. 10. May 15, 2002. pp. 8195-8197.

Del Monte, F., et al. Formation of $\gamma$-Fe2O3 Isolated Nanoparticles in a Silica Matrix. Langmuir. vol. 13, No. 14. 1997. pp. 3627-3634.

Sunil, D., et al. Iron and iron oxide particle growth in porous Vycor glass; correlation with optical and magnetic properties. Journal of Non-Crystalline Solids. vol. 319. 2003. pp. 154-162.

Okamoto, S., et al. Size dependencies of magnetic properties and switching behavior in FePtL1$_0$ nanoparticles. Physical Review B. vol. 67. 2003. pp. 094422-1-094422-7.

Guzman, Maribel, et al. Morphologic and magnetic properties of $Pd_{100-x}Fe_x$ nanoparticles prepared by ultrasound assisted electrochemistry. Journal of Applied Physics. vol. 92, No. 5. Sep. 1, 2002. pp. 2634-2640.

Yao, Y.D., et al. Magnetic and thermal studies of nano-size Co and Fe particles. Journal of Magnetism and Magnetic Materials. vol. 239. 2002. pp. 249-251.

Shen, C.M., et al. Synthesis and characterization of *n*-octadecayl mercaptan-protected palladium nanoparticles. Chemical Physical Letters. vol. 373. 2003. pp. 39-45.

Chen, Shaowei, et al. Alkanethiolate-Protected Palladium Nanoparticles. Chem. Mater. vol. 12. 2000. pp. 540-547.

Schmid, Gunter, et al. $Pt_{309}Phen_{36}O_{30\pm10}$, a Four-Shell Platinum Cluster. Agnew. Chem. Int. Ed. Engl. vol. 28., No. 6. 1989. pp. 778-780.

Bradley, John S., et al. Surface Chemistry on Colloidal Metals: A High-Resolution Nuclear Magnetic Resonance Study of Carbon Monoxide Adsorbed on Metallic Palladium Crystallites in Colloidal Suspension. J. Am. Chem. Soc. vol. 113. 1991. pp. 4016-4017.

Bonnemann, Helmut, et al. Formation of Colloidal Transition Metals in Organic Phases and Their Application in Catalysis. Agnew. Chem. Int. Ed. Engl. vol. 30. 1991. pp. 1312-1314.

Brown, Kenneth R. Hydroxylamine Seeding of Colloidal Au Nanoparticles in Solution and on Surfaces. Langmuir. vol. 14. No. 4. 1998. pp. 726-728.

Pillai, Zeena S., et al. What Factors Control the Size and Shape of Silver Nanoparticles in the Citrate Ion Reduction Method? J. Phys. Chem. B. vol. 108. 2004. pp. 945-951.

Brust, Mathias, et al. Synthesis of Thiol-derivatised Gold Nanoparticles in a Two-phase Liquid-Liquid System. J. Chem. Soc., Chem. Commun. 1994. pp. 801-802.

Reetz, Manfred, et al. Redox-Controlled Size-Selective Fabrication of Nanostructured Transition Metal Colloids. Advanced Materials. vol. 11, No. 9. 1999. pp. 773-777.

Reetz, Manfred, et al. Visualization of Surfactants on Nanostructured Palladium Clusters by a Combination of STM and High-Resolution TEM. Science. vol. 267. 1995. pp. 367-369.

Thomas O'Mahony et al., "*Alkylthiol gold nanoparticles in open-tubular capillary electrochromatography*", Journal of Chromatography A, vol. 1004, pp. 181-193 (2003).

Mathias Brust et al., "*Some recent advances in nanostructure preparation from gold and silver particles: a short topical review*", Colloids and Surfaces, A: Physicochemical and Engineering Aspects, vol. 202, pp. 175-186 (2002).

F. Sbrana et al., "*Assembling thiolated gold nanoparticles in compact patterns: a transmission electron microscopy and scanning probe microscopy investigation*", Materials Science and Engineering, B96, pp. 193-198 (2002).

Anita Swami et al., "*Water-dispersible nanoparticles via interdigitation of sodium dodecylsulphate molecules in octadecylamie-capped gold nanoparticles at a liquid-liquid interface*", Proc. Indian Acad. Sci. (Chem. Sci.), vol. 115, Nos. 5 & 6, pp. 679-687 (2003).

Dormann, J.L. Le phenomene de superparamagnetisme. Revue de Physique Appliquee. vol. 16. 1981. pp. 275-301 (Abstract, Table IV and Figure 12 which are in English).

\* cited by examiner a)  b)

MAGNETIC NANOPARTICLES COMPRISING A CORE FORMED FROM NOBLE METALS

This is a continuation of International Application No. PCT/ES2005/070035, filed Mar. 23, 2005.

SECTOR OF THE ART

The object of this invention falls within nanotechnology applications. Magnets of very small dimensions (<5 nm) are provided in a range in which standard ferromagnetic metals behave as superparamagnetic entitles (disappearance of hysteresis cycle). It is first of all proposed to reduce the dimensions in magnetic recordings by using the developed nanoparticles. Applications are likewise proposed in biomedicine, as tools for biomolecule recognition, in nuclear magnetic resonance imaging, drug-release control or hyperthermia treatments.

OBJECT OF THE INVENTION

The object of this invention consists of nanoparticles of noble metals, with a controlled microstructure leading to the appearance of magnetic behaviour therein.

Equally constituting the object of this invention is a process for preparation of said nanoparticles.

STATE OF THE ART

The appearance of ferromagnetism in noble metals failing to meet the Stoner condition (N. Takano, T. Kai, K. Shiiki, F. Terasaki, Solid State Común. 97 (1996) 153) is a phenomenon which has so far been reported in the case of nanoparticles of palladium and has been attributed to confinement phenomena due to small size, surface anisotropy owing to the high surface/volume ratio in a nanoparticle and/or anisotropy introduced into the edges of twin crystals in twinned nanoparticles (B. Sampedro, P. Crespo, A. Hernando, R. Litrán, J. C. Sánchez-López, C. López-Cartes, A. Fernández, J. Ramírez, J. González-Calbet, M. Vallet, Phys. Rev. Let 91 (2003) 237203-1; T. Sinohara, T. Sato, T. Taniyama, Phys. Rev. Let. 91 (2003) 197201; T. Taniyama, E. Ohta, T. Sato, Phys. B 237 (1997) 286; E. Huger, K. Osuch, Europhys. Let. 63 (2003) 90; V. Kumar, Y. Kawazoe, Phys. Rev. B 66 (2002) 144413). In these works the sizes of the nanoparticles reported are in the range 2-15 nm. Some previous works also point to the possible existence of ferromagnetism in Au (H. Hori, T. Teranishi, M. Taki, S. Yamada, M. Miyake, Y. Yamamoto, J. Mag. Mag. Mat. 226 (2001) 1910) though no hysteresis cycles have been reported.

Nanoparticles of Au/Fe have also been reported consisting of an iron core and a crust of gold, functionalised with thiols or protected by surfactants (B. Ravel, E. E. Carpenter, V. G. Harris, J. of Appl. Phys. 91 (2002) 8195). The magnetic behaviour of the iron core gives rise to the appearance of superparamagnetism in these nanoparticles, and the proposal of possible applications in biomedicine (WO03072830, EP1339075, WO03057175). Likewise, nanoparticles of gold have been reported functionalised with organic radicals which confer a magnetic behaviour on the particles (EP1211698).

For nanoparticles of typically magnetic metals and oxides such as the metals Fe, Go, Ni and their magnetic oxides, there are numerous works and patents (F. del Monte, M. P. Morales, D. Levy, A. Fernández, M. Ocaña, A. Roig, E. Molins, K. O'Grady, C. J. Sema, Langmuir 13 (1997) 3627; D. Sunil, H. D. Gafney, M. H. Rafailovich, J. Non-Cryst. Solids (2003) 319; S. Okamoto, O. Kitakani, N. Kkuchi, Phys. Rev. B 67 (2003); M. Guzman, J. L Delplancke, G. J. Long, J. Appl. Phys. 92 (2002) 2634; Y. D. Yao, Y. Y. Chen, S. D. F. Lee, J. Magn. Magn. Mater. 239 (2002) 249, JP2003132519). Nevertheless, in standard ferromagnetic materials for particle sizes of the order of 5 nm or less, the ferromagnetic behaviour disappears, which eliminates the appearance of the hysteresis cycle and coercivity. This currently limits the possibility of increasing the density of information in magnetic recording (J. L. Dormann, Revue Phys. Appl. 16 (1981) 275).

The preparation of metallic nanoparticles protected by functionalisation (C. M. Shen, Y. K. Su, H. T. Yang, T. Z. Yang, H. J. Gao, Chem. Phys. Lett. 373 (2003) 39; S. Chen, K. Huang, J. A. Stearns, Chem. Mater. 12 (2000) 540) or using a surfactant (G. Schmid, B. Morun, J. O. Malm, Angew. Chem. 101 (1989) 772; J. S. Bradley, J. M. Miller, E. W. Hill, J. Am. Chem. Soc. 113 (1991) 4016; H. Bonnemann, W. Brijoux, R. Brikmann, E. Dinjus, T. Joussen, B. Korall, Angew. Chem. 103 (1991) 1344; K. R. Brown, M. J. Natan, Langmuir 14 (1998) 726, Z. S. Pilla, P. V. Kamat, J. Phys. Chem. B 108 (2004) 945) are widely reported processes. In particular, the preparation of gold nanoparticles by reduction of a metal salt with borohydride and functionalised with thiol type derivatives is a well-established method (M. Brust, M. Walker, D. Bethell, D. Schriffin, R. Whyman, J. Chem. Soc., Chem. Commun. (1994) 801; Patent WO0232404). Likewise, the stabilization of palladium nanoparticles with salts of quaternary ammonium has also been reported (M. T. Reetz, M. Maase, Adv. Mater. 11 (1999) 773, M. Reetz, W. Helbig, S. A Quaiser, U. Stimming, N. Breuer, R. Vogel, Science 20 (1995) 367).

The present invention has adapted the reported methods for preparation of nanoparticles of Au and Pd functionalised with thiols in order to prepare particles of very small size (<5 nm in diameter). In particular, the obtaining of metallic cores surrounding or embedded in phases modified by a metal-sulphur covalent bond is controlled. A magnetic behaviour for these nanoparticles has been found which in some cases reaches up to room temperature with magnetizations of the order of 1 emu per gram of metal.

EXPLANATION OF THE INVENTION

The object of this invention consists of magnetic nanoparticles of noble metals non-magnetic in the mass state, of size less than 5 nm comprising:

a) a core formed from a noble metal and
b) an anisotropic crust formed from compounds containing at least one metal-sulphur covalent bond.

The size of the nanoparticles preferably lies between 1.0 and 2.0 nm, more preferably between 1.2 and 1.4 nm.

The noble metal for the core is Au, Pd, Pt, Ag or any other metal non-ferromagnetic in the mass state. When the core is formed from Au or Pd, the anisotropic crust contains Au—S/Pd—S compounds and Au—S—R/Pd—S—R compounds in proportions between 1/1000 and 1000/1 (Au—S/Au—S—R or Pd—S/Pd—S—R).

R is an aliphatic chain in turn joined to other molecules, in particular proteins or other biomolecules.

The magnetic nanoparticles of the present invention can display a ferromagnetic behaviour, a ferromagnetic behaviour with low coercive field or a paramagnetic behaviour.

Likewise constituting an object of the present invention is a procedure for preparation of said magnetic nanoparticles which comprises the reaction of a precursor of the non-ferromagnetic noble metal with a thiol derivative of general formula HS—R in stoichiometric excess and in the presence of a reducing agent. When the non-magnetic noble metal is gold the precursor is prepared by means of reaction of tetrachloroauric acid with any quaternary ammonium salt in stoichiometric excess. When the non-magnetic noble metal is palladium the precursor is prepared by means of reaction of any palladium salt, in particular nitrate, sulphate or chloride, with any quaternary ammonium salt in stoichiometric excess.

Finally, likewise constituting an object of the present invention is the use of said magnetic nanoparticles in various fields:
- increase in the density of information in a magnetic recording
- development of diagnostic techniques in biomedicine.
- controlled release of drugs
- hyperthermia treatment
- improving the imaging in nuclear magnetic resonance
- biosensors and biochips
- magnetic printing
- magneto-optical applications
- coding

DETAILED DESCRIPTION OF THE INVENTION

Figure 1:
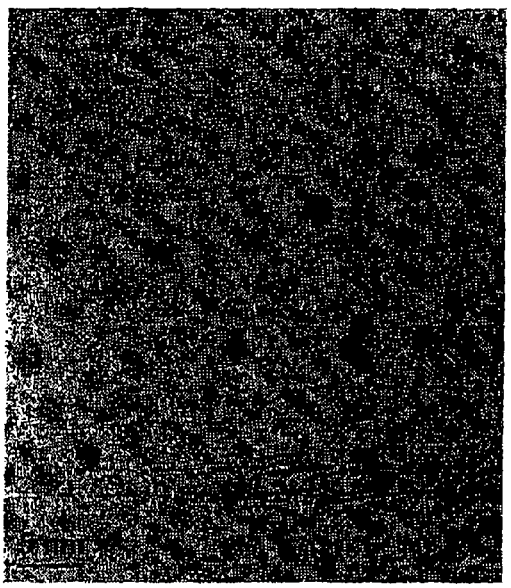
FIG. 1: Micrographs obtained by transmission electron microscopy of: a) nanoparticles of gold functionalised with dodecanethiol, b) nanoparticles of palladium functionalised with dodecanethiol.
Figure 1:
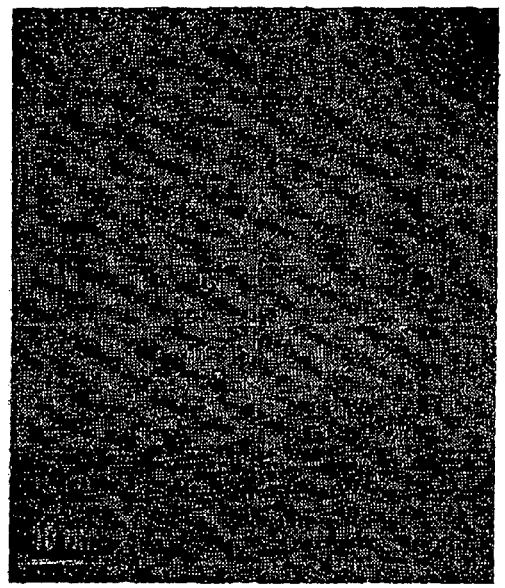

The object of the present invention consists of nanoparticles in which the appearance is observed of magnetic behaviour. The nanoparticles are of noble metals, in particular gold and palladium, modified in such a way that a microstructure is produced of the core-crust or "nanocomposite" type, which in turn gives rise to a strong surface anisotropy due to covalent bonds or interaction with dipoles. The attaining of the desired magnetic properties is in all cases based on the preparation of colloidal nanoparticles (see FIG. 1) of noble metals by reduction of precursor salts according to various conditions:

i) Reduction of gold or palladium salts in the presence of thiol derivatives of various organic compounds of the type R—SH. R is generally an aliphatic chain. The reducing agent is borohydride. The reaction is carried out in an excess of thiol derivative in order to achieve the desired microstructure.

ii) Reduction of gold or palladium salts in aqueous medium in the presence of water soluble thiol derivatives. Similar to the method described in i).

Figure 2:
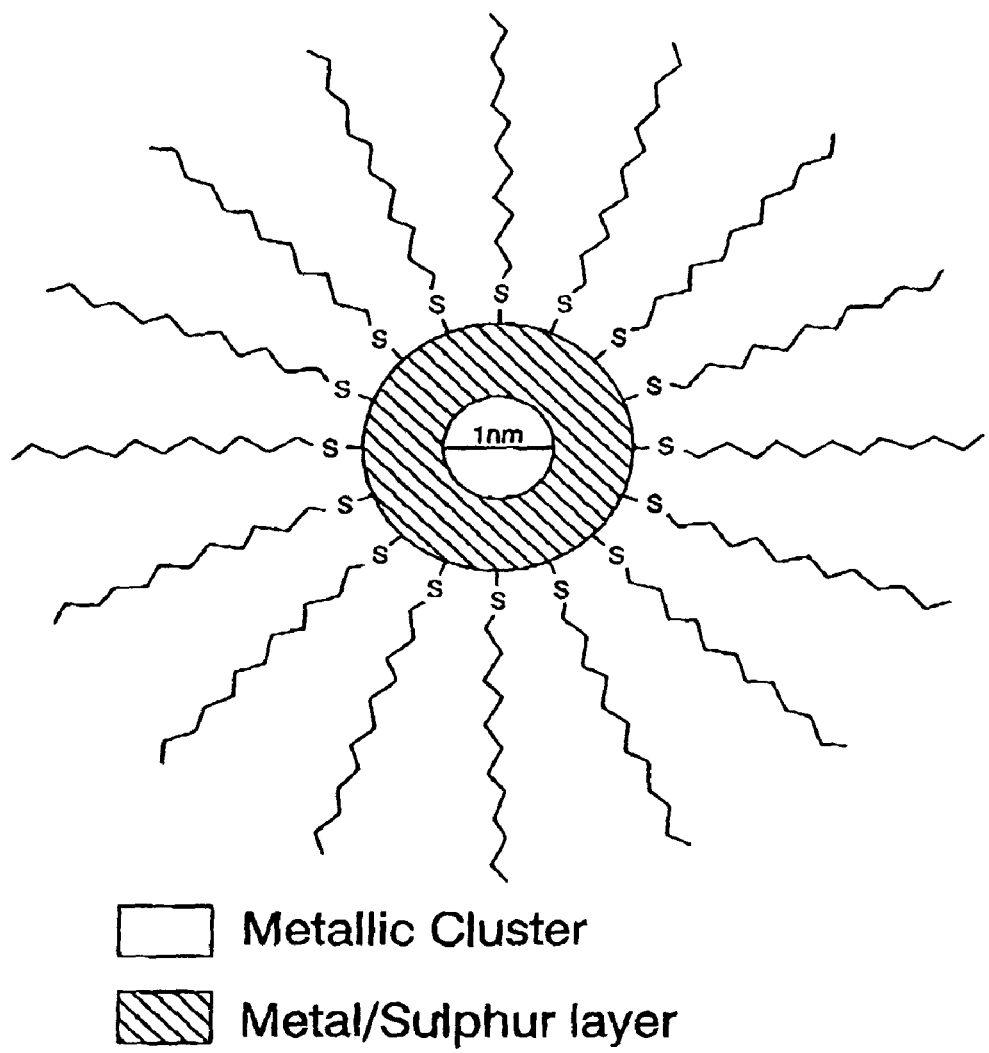
FIG. 2: Diagram of the microstructure of a nanoparticle of diameter 1.4 nm functionalised with dodecanethiol. The metallic nanoparticle is formed from a core crust structure.

The methods described using the conditions for the generation of very small size nanoparticles produce a microstructure formed from a metallic core (<5 nm) and a crust containing metal-sulphur covalent bonds (see FIG. 2). The presence of this crust, or the presence of surface dipoles, gives rise to a strong anisotropy in these particles. The preparation conditions must be exact in order to achieve the desired microstructure. In the case of gold and palladium, the ferromagnetic behaviour appears by functionalisation with thiol derivatives.

Figure 3:
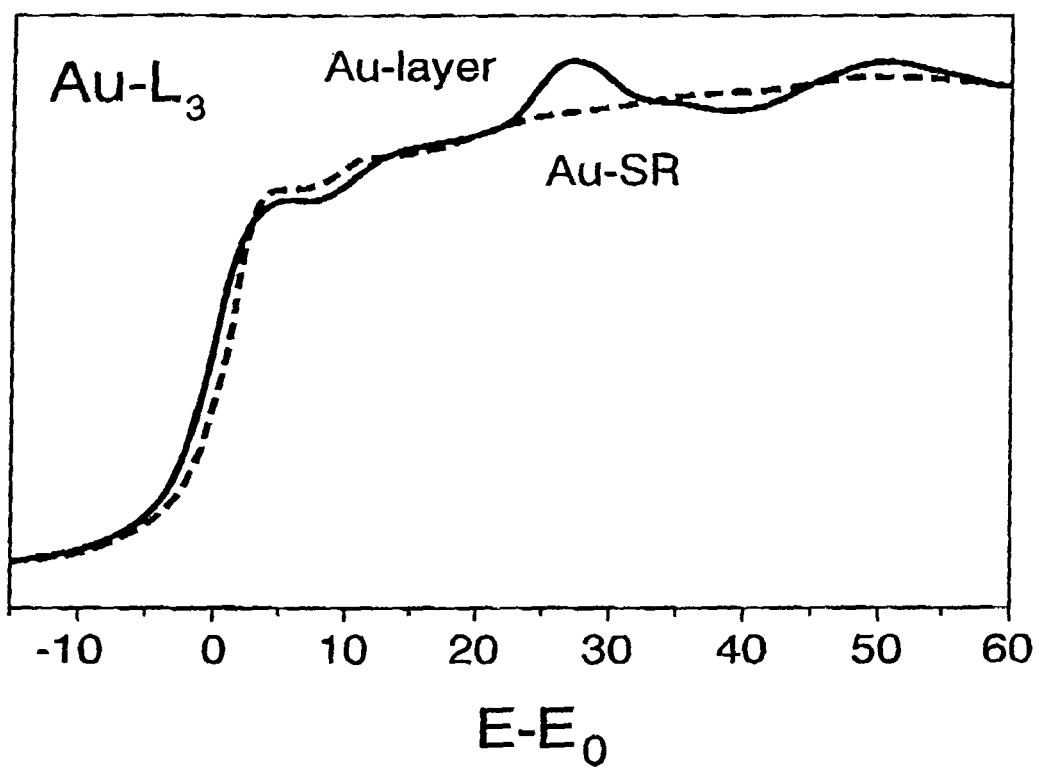
FIG. 3: XANES spectra for conventional gold leaf (gold leaf) and for a sample of nanoparticles of gold functionalised with thiol (Au—SR).
Figure 4:
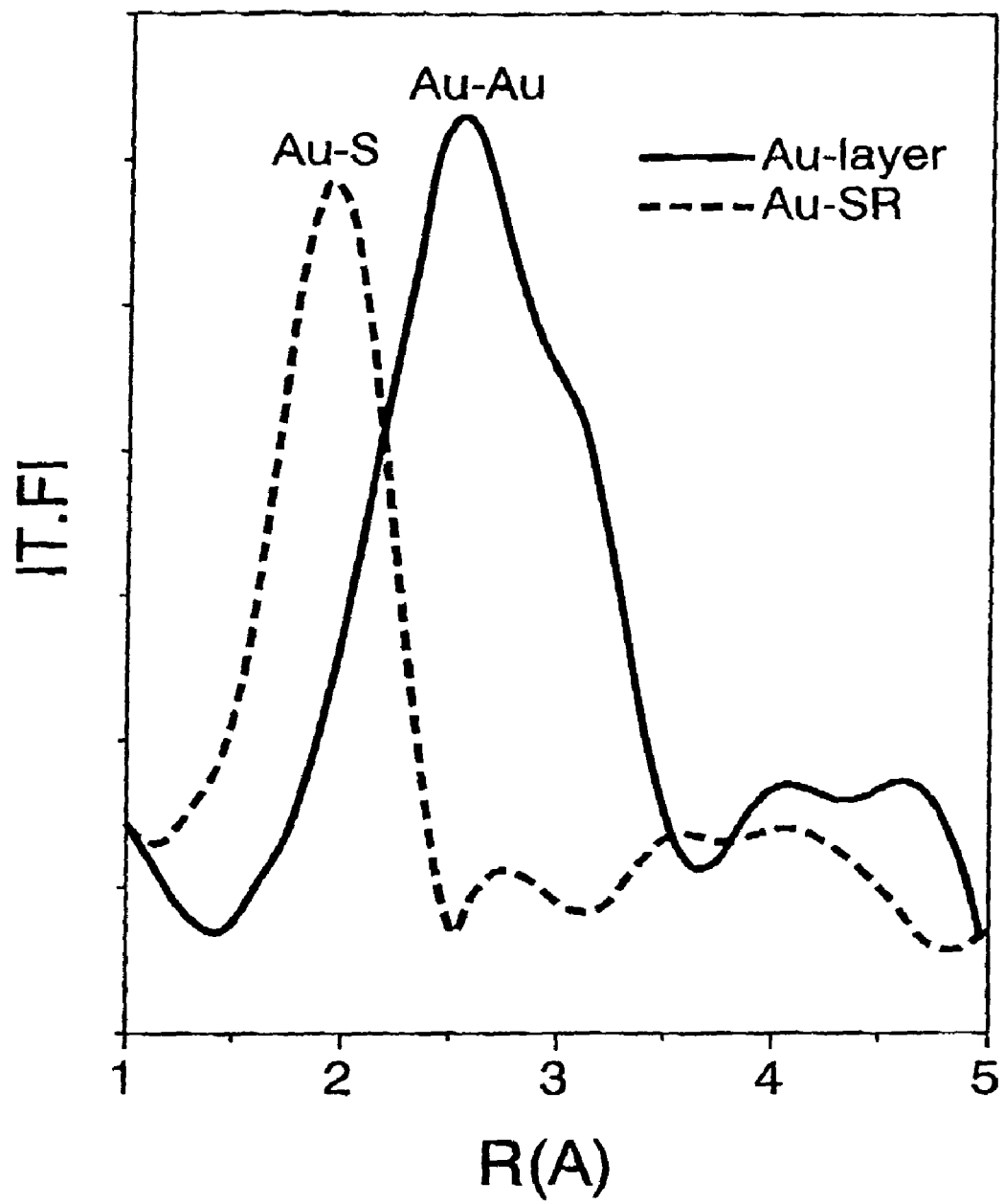
FIG. 4: Fourier transforms of EXAFS oscillations for conventional gold leaf (gold leaf) and for a sample of nanoparticles of gold functionalised with thiol (Au—SR).
Figure 5:
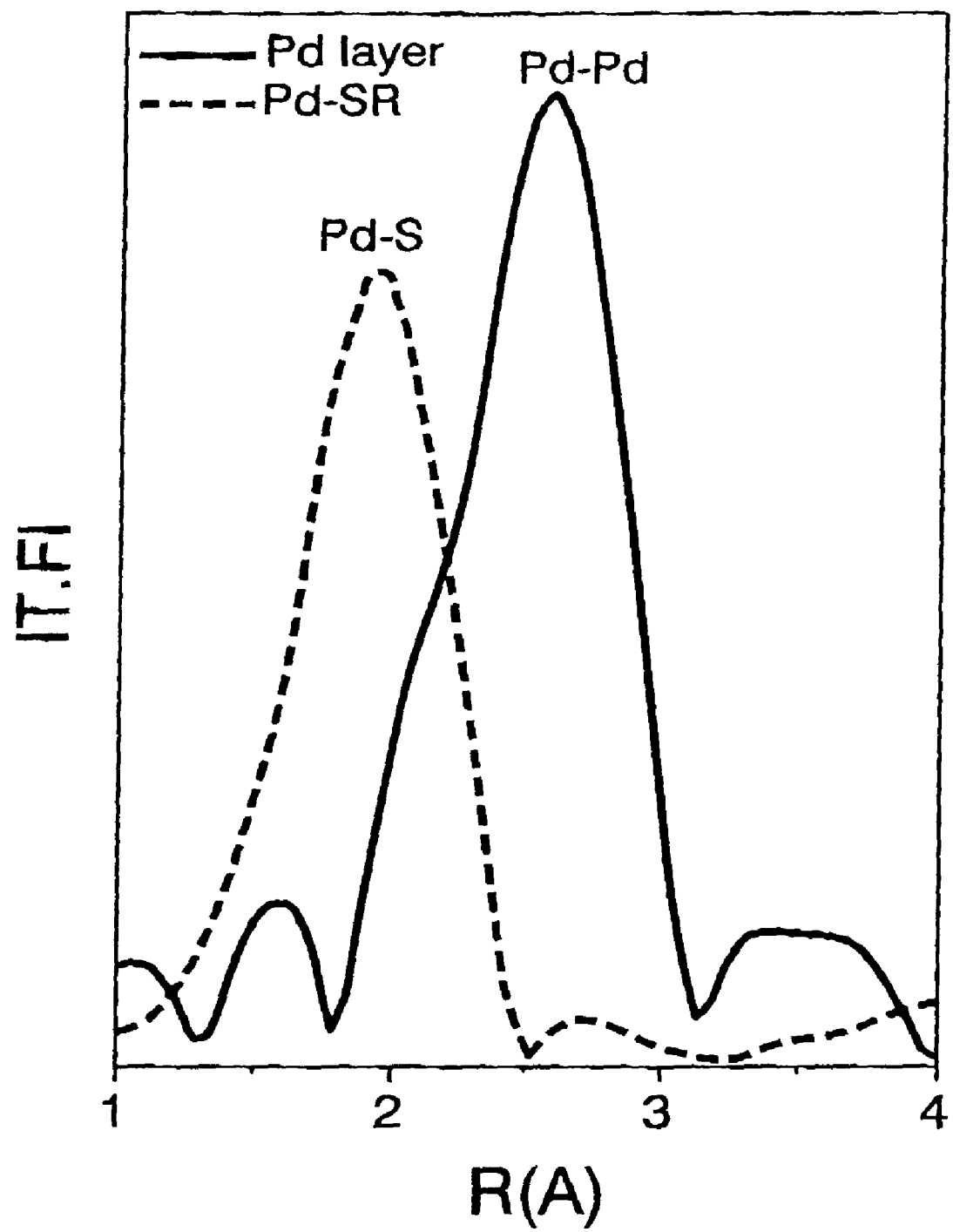
FIG. 5: Fourier transforms of EXAFS oscillations for conventional palladium leaf (palladium leaf) and for a sample of nanoparticles of palladium functionalised with thiol (Pd—SR).

A fundamental parameter permitting the microstructures of the generated nanoparticles to be assessed is the X-ray absorption spectrum. In the case of nanoparticles of gold functionalised with thiols, the spectrum close to the threshold (XANES) for the $L_3$ border of the gold shows the charge transfer of level $5d$ of the Au to the S, which is necessary for the appearance of the ferromagnetic behaviour in these particles (see FIG. 3). Likewise, FIG. 4 contains the Fourier transform of the EXAFS oscillations indicating the presence of an extremely small metallic core and the presence of a modified layer of gold covalently bonded to sulphur. In the case of nanoparticles of palladium functionalised with thiols, the Fourier transform of the EXAFS oscillations is shown in FIG. 5 for the K border of the Pd. In a similar way to the case with gold, the spectrum indicates the presence of an extremely small metallic core and the presence of a palladium phase bonded to sulphur. In both cases, the phenomenon is greater (greater coercive field, greater magnetization) the greater the metallic aggregate, and the interaction with the modified layer of metal is also necessary.

Figure 6:
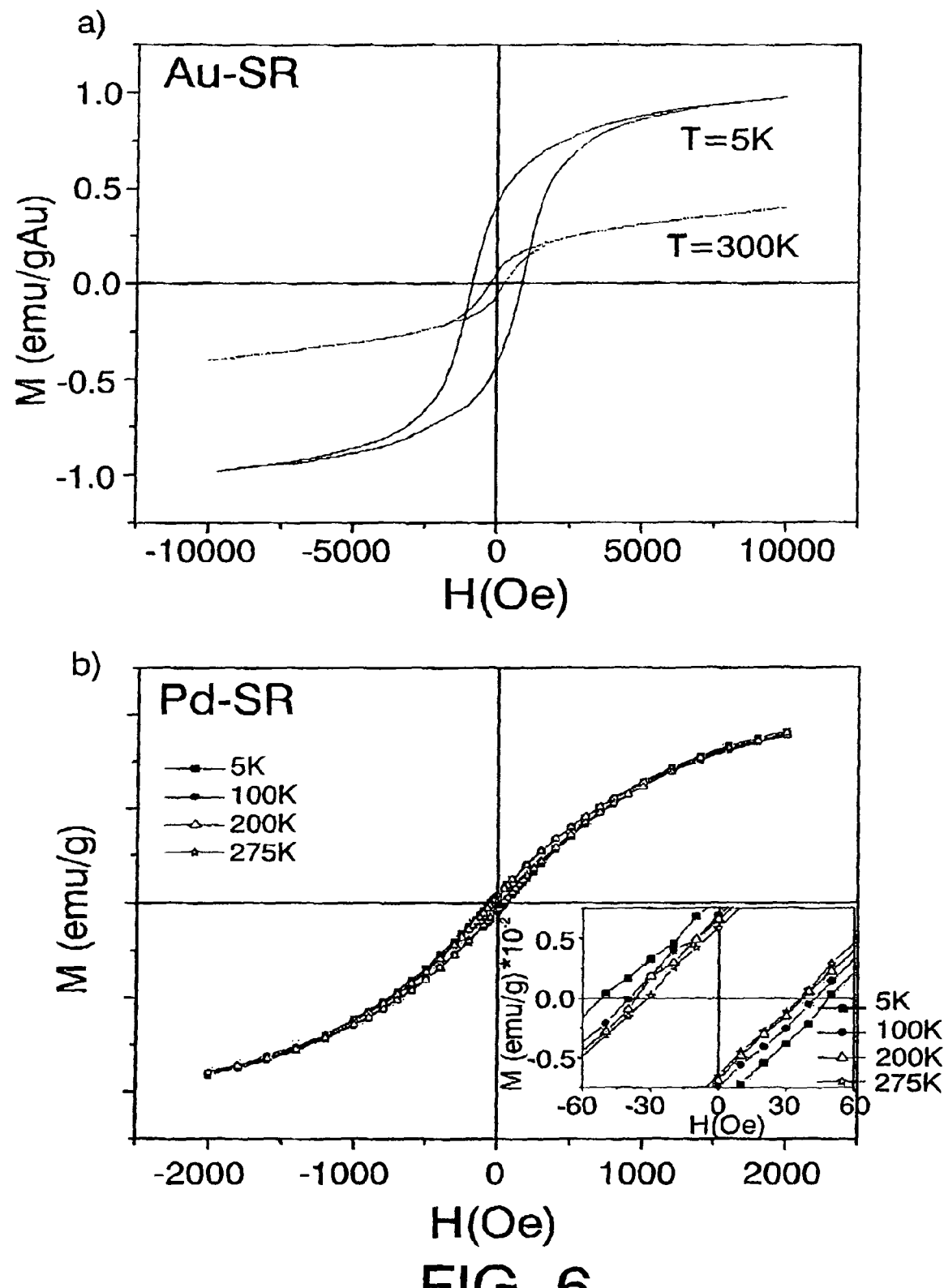
FIG. 6: Hysteresis cycle for: a) nanoparticles of gold functionalised with thiol derivatives measured at room temperature and at 5 K; b) nanoparticles of palladium functionalised with thiol derivatives measured at different temperatures.

The phenomenon of the appearance of the hysteresis cycle can, depending on the sample, be extended to room temperature and reach coercive fields of 860 Oe and magnetizations of 1 emu/g of metal at temperatures of 5 K (see FIG. 6).

Various specific cases have been characterised and described of magnetic nanoparticles of noble metals that are non-magnetic in the mass state:

i) Nanoparticles of gold functionalised with thiols. Nanoparticles of diameter 1.4 nm as observed by transmission electronic microscopy (see FIG. 1). This inorganic part could be modelled as consisting of a core of 13 atoms of gold surrounded by 30 atoms of gold bonded to 20 atoms of interstitial sulphur. These 30 atoms of gold are all surface atoms and are linked to 30 chains of dodecanethiol via atoms of sulphur covalently bonded to gold (see FIG. 2). At room temperature, these particles display a magnetization of 0.4 emu/g and a coercive field of 250 Oe. At 5 K the saturation magnetization reaches the value of 1 emu/g, with the coercive field being 860 Oe (see FIG. 6).

ii) Nanoparticles of palladium functionalised with thiols. Nanoparticles of diameter 1.2 nm embedded in an amorphous mass as observed by transmission electronic microscopy (see FIG. 1). The microstructure of the nanoparticles is again made up of a very small metal core surrounded by a layer of PdS. The polymer mass in which the particles are embedded consists of Pd—S bonds with some thiol chains. These particles display a saturation magnetization of 0.15 emu/g and a coercive field with values from 30 Oe at 275 K up to 50 Oe at 5 K (see FIG. 6).

iii) Nanoparticles of gold and palladium with diameters of the order of 2 nm or more functionalised with thiols. They display the phenomenon with less magnetization and smaller coercive fields in comparison with particles of less than 2 nm. In these cases the microstructure is more typical of a pure metallic core with the metal atoms of the surface bonded to the organic chain via sulphurs.

In some nanoparticles, the appearance of resonance plasmons in the UV-VIS absorption spectrum tells us of the appearance of electron delocalisation phenomena; while in others the absence of plasmons indicates the localisation of holes and electrons. The physical mechanisms of the appearance of the magnetic behaviour has to be different in both types of particle. For particles with plasmons, the Stoner ferromagnetism condition is produced as a consequence of the increase in density of states in the Fermi level. For particles without plasmons, the localisation of the density of holes produced by electron transfer of d levels of the metal (Au or Pd) to sulphur atoms has to play a fundamental role.

No kind of ferromagnetic behaviour has been observed in macroscopic samples of palladium sulphide.

In terms of the use of the magnetic nanoparticles of the present invention, some possible applications are described below:

Use in Devices for the Controlled Release of Drugs

The nanoparticles of the present invention can be employed instead of radioactive materials used as tracers for the release of drugs.

The use of these magnetic nanoparticles in place of radioactive substances permits the release of a drug to be monitored by means of measuring the variations in magnetic properties, thus eliminating the harmful effects of radiation.

In addition, the magnetic nanoparticles can be used in vaccination guns as an alternative to vaccine impellers, usually compressed air or gas (particularly helium), which cause pain and marks on the skin. The impelling power would in this case by provided by the application of a magnetic field, which would cause the acceleration of the nanoparticles as they pass through the epidermis.

Use for Hyperthermia Treatments

An external AC magnetic field is applied for locally heating a region (for example a tumour zone) in which the magnetic nanoparticles have been deposited or accumulated. The supplied preparation can, as well as the metallic core, also contain specific ligands which can in turn be medicines or they can favour the accumulation of the nanoparticles in a specific tissue.

The system would consist of an AC magnetic field generator perpendicular to the axial direction of the patient. The system would have an AC frequency also adjustable in the 100 kHz range and a variable field strength from 0 to 15 kA/m. Similar systems have been proposed for nanoparticles of ferromagnetic materials in the mass state (see for example A. Jordan et al., J. Mag. Mag. Mat. 225 (2001) 118-126).

The magnetic nanoparticles of noble metals would have major advantages owing to their very small size, the biocompatible nature of gold and the possibility of carrying out a functionalisation made to measure for each type of treatment, tumour type, etc.

Use for Improving Imaging in Magnetic Resonance (MR)

The magnetic nanoparticles of noble metals can be used for improving the imaging in MR.

MR images in some cases lack sufficient contrast for permitting an efficient viewing of structures such as tumours.

Such images can be improved using magnetic nanoparticles as the contrast medium, which would allow, for example, the detection of tumours that are small size and therefore with better possibilities of treatment.

The magnetic nanoparticles of the present invention having noble metals such as Au or Pd in their core are especially useful for this application since the metals in the elemental state are better contrast agents than oxides of those same metals.

In addition, these nanoparticles have a better biocompatibility than do other nanoparticles, for example Au+Fe in the core.

Use as Biosensors and Biochips

Figure 7:
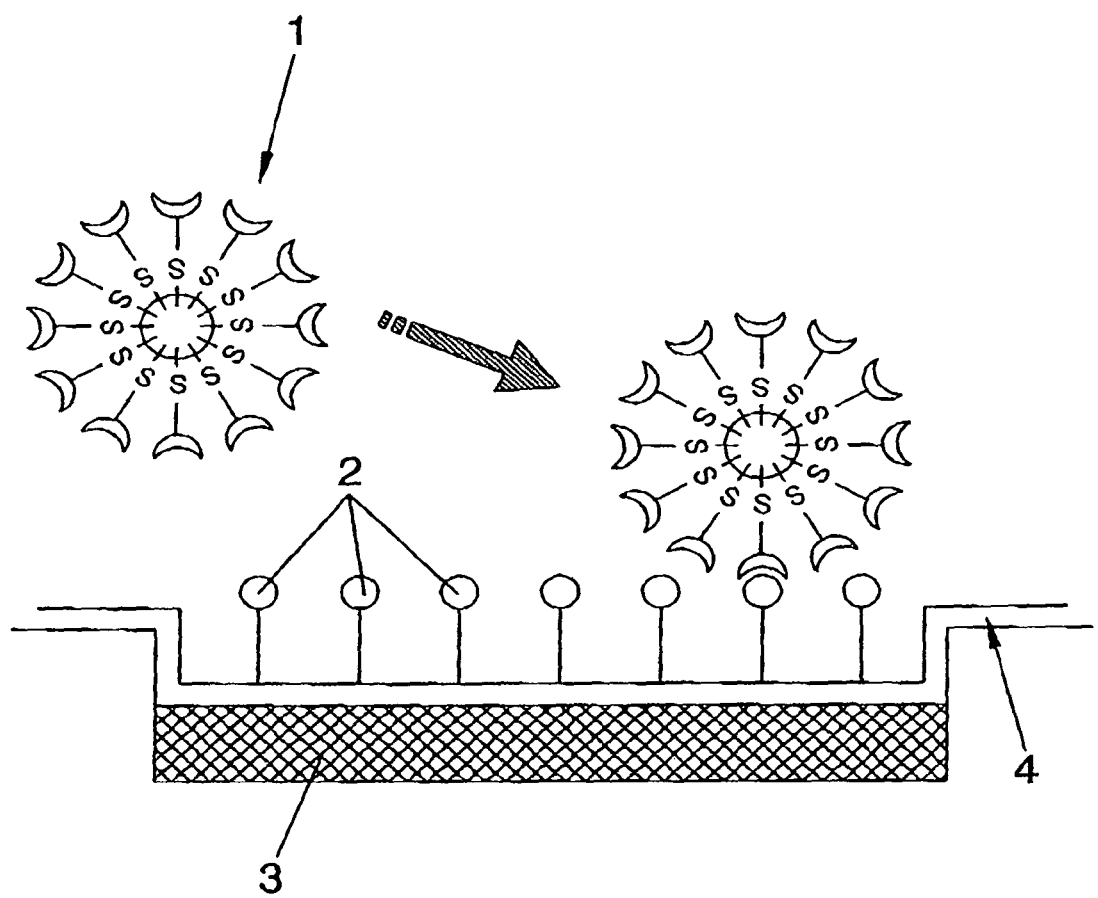
FIG. 7: Diagram of a biosensor device based on magnetic nanoparticles.

FIG. 7 illustrates a diagram of a biosensor device based on magnetic nanoparticles functionalised with type A ligands (1). When the type A ligands recognise the type B biomolecule (2), the nanoparticle becomes attached and a signal is detected in the magnetic sensor (3) which is separated from the nanoparticles by a protective passivation layer (4). An array of devices like that represented in the diagram could be ordered forming a biochip type unit in which each magnetoresistive sensor could read the signal corresponding to one component of an array of biomolecules.

Use for Increasing the Density in Magnetic or Magneto-Optics Recordings

An ordered distribution of magnetic nanoparticles of noble metals on a support serves as the basis for the manufacture of compact discs using magnetic fields for storing data. The reading of the information can in turn be done with a magnetic sensor (magnetoresistive type) or by the Kerr effect using a laser.

Use in Magnetic Printing and Coding

The magnetic nanoparticles of noble metals are processed and stored in the form of a powder. The precursor powder is used in preparations of colloidal solutions (ferrofluids). By varying the functionalisation of the nanoparticle, ferrofluids are manufactured in different types of solvent: organic or aqueous. The magnetic ink is processed in magnetic printing, writing of bar codes, etc.

MODE OF EMBODIMENT OF THE INVENTION

Two examples of embodiment of the invention consist of the preparation, microstructural characterisation and recording of the ferromagnetic behaviour of nanoparticles of gold and palladium modified with thiol derivatives.

EXAMPLE 1

Ferromagnetic Behaviour in Nanoparticles of Gold Functionalised with Chains of Dodecanethiol To a solution of 0.11 g of 98% tetraoctylammonium bromide ($N(C_8H_{17})_4Br$ (Aldrich) in 20 ml of toluene previously dried and degasified, are added 0.075 g of tetrachloroauric acid ($HAuCl_4$, 99%, Aldrich) dissolved in 7.5 ml of Milli-Q water (the molar ratio of the ammonium salt with respect to the gold salt is 2). The mixture is subjected to strong magnetic stirring at room temperature for 30 minutes, until all the gold precursor has been extracted from the aqueous phase to the organic phase. The aqueous phase is separated in a decanting funnel and discarded. To the organic phase, subjected to vigorous magnetic stirring, is added 0.1 ml of dodecanethiol (the molar ratio of the dodecanethiol with respect to the gold precursor is 2) and then drop by drop a solution of 0.09 g of sodium borohydride is added ($NaH_4B$, 99%, Aldrich) dissolved in 6.25 ml of Milli-Q water (the reducing agent is added in excess, 11.7 mols of the agent with respect to the gold precursor) It is observed that after a few seconds the solution, which was previously orange, takes on an intense black coloration owing to the formation of metallic cores. After 1 hour of strong magnetic stirring, the aqueous phase is again discarded with the aid of a decanting funnel. The toluene in the solution obtained is eliminated by means of a rotovapor, and the metallic particles are then precipitated in 200 ml of absolute ethanol. This dispersion is subjected to a temperature of −20° C. for 8 hours and filtered using a millipore filter of pore size 0.1 microns. The precipitate remaining on the filter is again redissolved in toluene, precipitated in absolute ethanol and filtered. This process is repeated three times with the aim of eliminating remains of dodecanethiol and possible impurities.

The X-ray absorption spectrum is recorded for the nanoparticles obtained by the process described above, with the Fourier transform shown in FIG. 4 being obtained. The obtaining of this spectrum shows the appearance of the microstructure formed by an extremely small metal core and a crust consisting of gold covalently bonded to sulphur. This microstructure is a necessary condition for the appearance of ferromagnetic behaviour in gold nanoparticles. The hysteresis cycle is recorded at 5 K and at room temperature (see FIG. 6). At room temperature, magnetization values of 0.4 emu/g and a coercive field of 250 Oe are obtained. At 5 K the saturation magnetization reaches the value of 1 emu/g, with the coercive field being 860 Oe.

EXAMPLE 2

Ferromagnetic Behaviour in Nanoparticles of Palladium Functionalised with Chains of Dodecanethiol To a solution of 0.55 g of 98% tetraoctylammonium bromide ($N(C_8H_{17})_4Br$ (Aldrich) in 20 ml of toluene previously dried and degasified, are added 0.050 g of palladium nitrate ($Pd(NO_3)_2$, 99%, Aldrich) dissolved in 10 ml of a solution of Milli-Q water acidified with hydrochloric acid at a concentration of 0.5 N. The mixture is subjected to strong magnetic stirring at room temperature for 30 minutes, until all the palladium precursor has been extracted from the aqueous phase to the organic phase. The aqueous phase is separated in a decanting funnel and discarded. To the organic phase, subjected to vigorous magnetic stirring, is added 0.1 ml of dodecanethiol (the molar ratio of the dodecanethiol with respect to the palladium precursor is 2) and after 15 minutes of magnetic stirring a solution of 0.10 g is quickly added of sodium borohydride ($NaH_4B$, 99%, Aldrich) dissolved in 5 ml of Milli-Q water (the reducing agent is added in excess, 12 mols of the agent per mol of the palladium salt). It is observed that after a few seconds the solution, which was previously orange, takes on a dullish coloration owing to the formation of metallic cores. The reaction is carried out in a nitrogen atmosphere with the aim of avoiding possible reoxidations of the palladium. After 30 minutes of strong magnetic stirring, the aqueous phase is again discarded with the aid of a decanting funnel. The toluene in the solution obtained is eliminated by means of a rotovapor, and the metallic particles are then precipitated in 200 ml of methanol. This dispersion is filtered using a millipore filter of pore size 0.1 microns. The precipitate remaining on the filter is again redissolved in toluene, precipitated in methanol and filtered. This process is repeated three times with the aim of eliminating remains of dodecanethiol and possible impurities.

The X-ray absorption spectrum is recorded for the nanoparticles obtained by the process described above, with the Fourier transform shown in FIG. 5 being obtained. The obtaining of this spectrum shows the appearance of the microstructure formed by an extremely small metal core surrounded by a palladium phase covalently bonded to sulphur. This microstructure is a necessary condition for the appearance of ferromagnetic behaviour in palladium nanoparticles.

The hysteresis cycle is recorded at different temperatures (see FIG. 6). These particles display a saturation magnetization of 0.15 emu/g and a coercive field with values from 30 Oe at 275 K up to 50 Oe at 5 K.

The invention claimed is:

1. Magnetic nanoparticles of noble metals having a size of less than 5 nm, the nanoparticles comprising:
   a) a core formed from a noble metal and
   b) an anisotropic layer formed from compounds containing at least one metal-sulphur covalent bond wherein the nanoparticles display ferromagnetic behavior at room temperature and a hysteresis cycle, and further wherein the nanoparticles are formed from a non-ferromagnetic precursor noble metal.

2. Magnetic nanoparticles of noble metals according to claim 1, wherein the noble metal for the core is Au, Pd, Pt, or Ag.

3. Magnetic nanoparticles of noble metals according to claim 1, wherein the size of the nanoparticles lies between 1.0 and 2.0 nm.

4. Magnetic nanoparticles of noble metals according to claim 1, wherein when the core is formed from Au, the anisotropic layer contains Au—S compounds and Au—S—R compounds in proportions between 1/1000 and 1000/1 (Au—S/Au—S—R), wherein R is an aliphatic chain.

5. Magnetic nanoparticles of noble metals according to claim 4, wherein R is an aliphatic chain or an aliphatic chain in turn joined to other molecules, R being able to contain a marker, a fluorescent group or a radioactive isotope.

6. Magnetic nanoparticles of noble metals according to claim 5, wherein the other molecules are proteins or other biomolecules.

7. Magnetic nanoparticles of noble metals according to claim 1, wherein when the core is formed from Pd, the anisotropic layer contains Pd—S compounds and Pd—S—R compounds in proportions between 1/1000 and 1000/1 (Pd—S/Pd—S—R), wherein R is an aliphatic chain.

8. Magnetic nanoparticles of noble metals according to claim 7, wherein R is an aliphatic chain or an aliphatic chain in turn joined to other molecules, R being able to contain a marker, a fluorescent group or a radioactive isotope.

9. Magnetic nanoparticles of noble metals according to claim 8, wherein the other molecules are proteins or other biomolecules.

10. Magnetic nanoparticles of noble metals according to claim 1, wherein the size of the nanoparticles lies between 1.2 and 1.4 nm.

11. Biosensor which comprises the magnetic nanoparticles of claim 1 therein.

12. Magneto-optical device comprising the magnetic nanoparticles of claim 1 therein.

13. Coding device which comprises the magnetic nanoparticles of claim 1 therein.

14. A system which comprises a population of one or more of the nanoparticles according to claim 1.

15. A system according to claim 14 which comprises a plurality of nanoparticles containing different functional groups.

16. Process for preparation of magnetic nanoparticles according to claim 1, comprising the reaction of the non-ferromagnetic precursor noble metal with a stoichiometric excess of a thiol derivative of general formula HS—R, wherein R is an aliphatic chain, and in the presence of a reducing agent, under conditions such that the anisotropic layer contains metal-sulfur covalent bonds.

17. Process for preparation of magnetic nanoparticles according to claim 16, wherein when the non-ferromagnetic precursor noble metal is gold the precursor is prepared by means of reaction of tetrachloroauric acid with a stoichiometric excess of any quaternary ammonium salt.

18. Process for preparation of magnetic nanoparticles according to claim 16, wherein when the non-ferromagnetic precursor noble metal is palladium the precursor is prepared by means of reaction of a palladium salt comprising nitrate, sulphate or chloride, with a stoichiometric excess of a quaternary ammonium salt.

19. Method for increasing the density of information in a magnetic recording which comprises forming an ordered distribution of the magnetic nanoparticles of claim 1 on a support of the magnetic recording.

20. Method for controlled release of drugs which comprises employing the nanoparticles of claim 1 as tracers in a device for such release.

21. Method for hyperthermia treatment which comprises employing the nanoparticles of claim 1 in a region to be heated.

22. Method for improving the imaging in nuclear magnetic resonance which comprises employing the nanoparticles of claim 1 as a contrast medium.

23. Method for magnetic printing which comprises employing the magnetic nanoparticles of claim 1 as a powder in an ink-forming dispersion.

* * * * *